United States Patent
Wachsberg et al.

(10) Patent No.: US 10,285,927 B2
(45) Date of Patent: May 14, 2019

(54) ORAL CARE COMPOSITIONS

(71) Applicant: Apollo Laboratories Inc., Toronto (CA)

(72) Inventors: Richard Wachsberg, Toronto (CA); Charles Wachsberg, Toronto (CA); Joel Edwards, Toronto (CA); Derek Sanderson, Toronto (CA)

(73) Assignee: Apollo Laboratories Inc., Toronto, Ontario (CA)

( * ) Notice: Subject to any disclaimer, the term of this patent is extended or adjusted under 35 U.S.C. 154(b) by 0 days.

(21) Appl. No.: 15/230,098

(22) Filed: Aug. 5, 2016

(65) Prior Publication Data

US 2018/0036224 A1 Feb. 8, 2018

(51) Int. Cl.

| | |
|---|---|
| *A61Q 11/00* | (2006.01) |
| *A23L 2/60* | (2006.01) |
| *A23L 2/56* | (2006.01) |
| *A61K 8/60* | (2006.01) |
| *A61K 8/92* | (2006.01) |
| *A61K 8/49* | (2006.01) |
| *A61K 8/34* | (2006.01) |

(52) U.S. Cl.
CPC .............. *A61K 8/922* (2013.01); *A61K 8/347* (2013.01); *A61K 8/49* (2013.01); *A61K 8/60* (2013.01); *A61Q 11/00* (2013.01); *A61K 2800/30* (2013.01)

(58) Field of Classification Search
CPC .......... A61K 8/60; A61K 47/26; A61Q 11/00; A23L 2/60; A23L 27/86
See application file for complete search history.

(56) References Cited

U.S. PATENT DOCUMENTS

| | | | | |
|---|---|---|---|---|
| 5,100,650 | A | * | 3/1992 | Carlin ...................... A61K 8/43 424/49 |
| 9,125,841 | B2 | | 9/2015 | Queiroz et al. |
| 9,161,892 | B2 | | 10/2015 | Simon et al. |
| 2006/0263306 | A1 | * | 11/2006 | Pan ....................... A61K 8/0216 424/53 |
| 2014/0134114 | A1 | | 5/2014 | Krammer et al. |

FOREIGN PATENT DOCUMENTS

CA 2813343 4/2012

OTHER PUBLICATIONS

Vishnumurhy Vummaneni and Dheeraj Nagpai, "Taste Masking Technologies: An Overview and Recent Updates," International Journal of Research in Pharamceutical and Biomedical Sciences, 3(2):510-524, Jun. 2012.
Brown et al., "Mannitol and Sorbitol Catabolism in *Streptococcus mutans*," Arch Oral Biol., 18(1):117-126, Jan. 1973 (Abstract Only).
Gülzow et al., "Metabolism of the Sugar Substitute Xylite by Microorganisms of the Human Oral Cavity," Dtsch Zahnarztl Z., 33(3):185-188, Mar. 1978 (Abstract Only).

* cited by examiner

*Primary Examiner* — Tracy Liu
(74) *Attorney, Agent, or Firm* — Haukaas Fortius PLLC; Michael H. Haukaas

(57) ABSTRACT

The present disclosure relates to oral care compositions. In particular, the present disclosure relates to oral care compositions comprising sucralose and sodium saccharin, while being substantially free of other sugars or sugar alcohols.

14 Claims, No Drawings

ORAL CARE COMPOSITIONS

FIELD

The present disclosure relates to oral care compositions. In particular, the present disclosure relates to oral care compositions comprising sucralose and saccharin, while being substantially free of other sugars or sugar alcohols.

INTRODUCTION

Oral compositions, such as mouthwashes or oral rinses, generally contain large amounts of ethanol, which helps to solubilize anti-bacterial agents or other active ingredients present in the formulations. In addition, ethanol itself has anti-septic properties. However, the alcohol and many anti-bacterial agents taste bitter or harsh in the oral cavity. As a result, oral compositions containing such components often contain large amounts of sweeteners, such as sugars or sugar alcohols, to mask the bitter taste of the active ingredients in the compositions. However, many sugars and sugar alcohols are metabolized by the bacteria present in the mouth and can therefore cause cavities. There remains a need for oral compositions that are pleasant tasting, but that are effectively sugar-free and do not cause a proliferation of the cariogenic bacteria that cause cavities.

SUMMARY

The present disclosure relates to oral care compositions which do not cause or promote cavities (anticariogenic), wherein the compositions contain bitter or harsh tasting active agents. In particular, the present disclosure relates to oral care compositions comprising sucralose and saccharin, while being essentially free of other sugars or sugar alcohols, wherein the compositions contain bitter or harsh tasting active agents. Accordingly, in one embodiment, the present disclosure includes an anticariogenic oral care composition, comprising:
(i) water;
(ii) sucralose;
(iii) saccharin;
(iv) at least one active ingredient having a bitter taste, wherein the composition contains less than 5% (w/v) of a sugar or sugar alcohol.

In another embodiment of the disclosure, there is also included an anticariogenic oral care composition comprising
(i) water;
(ii) ethanol;
(ii) sucralose;
(iii) saccharin; and
(iv) an essential oil selected from eucalyptol, menthol, methyl salicylate, and thymol, or combinations thereof,
wherein the composition contains less than 5% (w/v) of a sugar or sugar alcohol.

In one embodiment, the saccharin and sucralose are present in a ratio of between about 2:1 to about 1:1, or about 2:1.

The present disclosure also includes a method for the prevention of cavities, comprising administering an effective amount of an anticariogenic oral composition to the oral cavity of a person in need thereof. In one embodiment, the compositions are sugar-free, and therefore, do not promote or cause cavities.

Other features and advantages of the present application will become apparent from the following detailed description. It should be understood, however, that the detailed description and the specific examples while indicating embodiments of the application are given by way of illustration only, since various changes and modifications within the spirit and scope of the application will become apparent to those skilled in the art from this detailed description.

DESCRIPTION OF VARIOUS EMBODIMENTS

(I) Definitions

Unless otherwise indicated, the definitions and embodiments described in this and other sections are intended to be applicable to all embodiments and aspects of the present application herein described for which they are suitable as would be understood by a person skilled in the art.

As used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this application and claim(s), the word "consisting" and its derivatives, are intended to be close ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "oral composition" or "oral care composition" as used herein refers to a product that is not intentionally swallowed, but is rather retained in the oral cavity for a time sufficient to contact substantially all of the dental surfaces and/or oral tissues for purposes of oral activity. After sufficient time, the composition is expelled from the oral cavity. The oral composition may be in the form of a mouthwash, or oral rinse, such that the compositions are liquid and containing varying amounts of water and/or alcohol. The compositions may also be dry powders that can be reconstituted in water to form mouthwashes or rinses.

The term "anticariogenic" as used herein refers to the property of the composition that it does not cause or promote cavities.

The term "sugar" as used herein refers to any sugar-based compound, such as a monosaccharide or disaccharide, which can be metabolized by bacteria naturally present in the oral cavity of subjects and produces acidic by-products causing dental caries or tooth decay, and includes for example, sucrose, fructose, lactose, glucose, etc.

The term "sugar alcohol" as used herein refers to polyalcohols that are derived from carbohydrates by reduction of the aldehyde or keto group, and that may be metabolized by bacteria in the oral cavity, such as sorbitol.

The term "polyhydric alcohol" as used herein means an alcohol compound having at least two hydroxyl moieties and having sweetening characteristics, such as glycerin.

The term "substantially free" as used herein with respect to the presence of sugars, sugar alcohols or polyhydric alcohols in the oral compositions means a quantity that is less than that which would cause or promote dental caries, cavities or tooth decay.

The term "active ingredient having a bitter taste" as used herein refers to any substance, compound or drug which has a therapeutic effect in the oral cavity, such as an anti-bacterial effect, anti-septic effect, anti-plaque effect, anti-gingivitis effect etc., and which has a bitter or unpleasant taste in need of taste-masking. In one embodiment, the therapeutic effect of the active ingredient is to freshen breath or reduce odors (halitosis) which can be caused by bacteria in the oral cavity.

The term "orally acceptable excipients" as used herein refers to any commonly used excipients in oral care compositions such as alcohols, surfactants, dyes, fragrances, flavoring agents, solvents, preservatives, polymers, binders, viscosity agents, emulsifiers, foaming agents etc.

The term "w/v" as used herein indicates the percentage by mass of an ingredient per total volume of a liquid composition.

(II) Sugar-Free Anticariogenic Oral Care Compositions

The present disclosure relates to oral care compositions which do not cause or promote cavities, wherein the compositions contain bitter, harsh or unpleasant tasting compounds, for which it is desirable to mask their taste. In particular, the present disclosure relates to antiocariogenic oral care compositions comprising sucralose and saccharin, while being essentially free of other sugars, sugar alcohols or polyhydric alcohols, wherein the compositions contain bitter or harsh tasting active agents. In one embodiment, as the compositions are substantially free from sugars or sugar alcohols, the compositions help to prevent cavities as fermentable compounds do not remain on the teeth after using the composition. In another embodiment, the combination of sucralose and saccharin provide a sweetness flavor profile for oral care compositions without the addition of other sweetening agents such as sugar and sugar alcohols which can eventually cause cavities, wherein the combination of sucralose and saccharin mask the unpleasant taste of bitter compounds. In another embodiment, the anticariogenic compositions further comprise an alcohol, such as ethanol, the taste of which is also masked by the combination of sucralose and saccharin.

In another embodiment, the anticariogenic oral care compositions of the present disclosure at least one active agent having a bitter taste which kills, or prevents growth of, bacteria within the oral cavity of a subject. In another embodiment, as the oral care compositions are substantially free of sweetening agents which can cause cavities, the compositions fight or prevent cavities by killing (or preventing the growth of) the bacteria within the oral cavity, and subsequently, once the composition is expelled from the oral cavity, does not leave any significant amount (or none at all) of cavity causing compounds. In one embodiment, the compositions of the disclosure help to prevent cavities.

Accordingly, in one embodiment, the present disclosure includes an anticariogenic oral care composition, comprising:

(i) water;
(ii) sucralose;
(iii) saccharin;
(iv) at least one active ingredient having a bitter taste, wherein the composition contains less than 5% (w/v) of a sugar or sugar alcohol.

In another embodiment, the composition contains less than about 2.0% (w/v), or less than about 1.0% (w/v), or less than about 0.5% (w/v), or less than about 0.1% (w/v) of a sugar or sugar alcohol. In another embodiment, the composition also contains less than about 5.0% (w/v), or less than about 2.0% (w/v), or less than about 1.0% (w/v), or less than about 0.5% (w/v), or less than about 0.1% (w/v) of a polyhydric alcohol, such as glycerin. In a further embodiment, the composition is substantially free of a sugar or sugar alcohol. In another embodiment, the composition is free of a sugar or sugar alcohol. In a further embodiment, the composition is substantially free of a polyhydric alcohol. In another embodiment, the composition is free of a polyhydric alcohol.

In one embodiment, the sugar alcohol is sorbitol, xylitol, or maltitol. In one embodiment, the sugar alcohol is sorbitol. In another embodiment, the polyhydric alcohol is glycerin or propylene glycol.

In one embodiment, sucralose has the following chemical structure

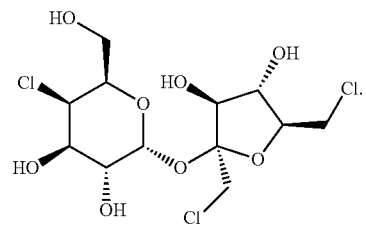 [SMILES: OC[C@H]1O[C@H](O[C@]2(CCl)O[C@H](CCl)[C@@H](O)[C@@H]2O)[C@H](O)[C@@H](O)[C@H]1Cl]

In one embodiment, saccharin has the following chemical structure

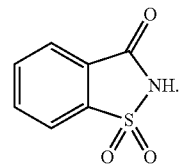 [SMILES: O=C1NS(=O)(=O)c2ccccc21]

In one embodiment, the saccharin is sodium saccharin.

In one embodiment, the saccharin and sucralose are present in a ratio of between about 5:1 to about 1:1. In another embodiment, the saccharin and sucralose are present in a ratio of between about 2:1 to about 1:1, or about 2:1 (saccharin:sucralose).

In another embodiment, the sucralose is present at an amount of less than 2.0% (w/v), or less than 1.0% (w/v), for example between about 0.001% to about 1.0% (w/v), or between about 0.01% to about 0.1% (w/v), or about 0.05% to about 0.1% (w/v). In a further embodiment, the saccharin is present at an amount of less than 2.0% (w/v), or less than 1.0% (w/v), for example between about 0.001% to about 1.0% (w/v), or between about 0.05% to about 0.2% (w/v), or about 0.1% to about 0.2% (w/v). In one embodiment, the saccharin is present in an amount of about 0.15% (w/v). In another embodiment, the sucralose is present in an amount of about 0.075% (w/v).

In another embodiment, the anticariogenic compositions of the disclosure comprise at least one active ingredient having a bitter or unpleasant taste for which it is desired to mask the taste of the ingredient. In one embodiment, the at least one active ingredient is a bitter-tasting anti-bacterial or anti-septic agent. In one embodiment, the active ingredient is an essential oil or compounds found in essential oils, or extract which may have anti-bacterial activity, for example, eucalyptol, menthol, methyl salicylate, thymol, tea tree oil, peppermint oil, *eucalyptus* oil, thyme oil, spearmint oil, wintergreen oil, grapefruit seed extract, or combinations thereof. In another embodiment, the essential oils are present in an amount of less than about 1.0% (w/v). In another embodiment, the essential oils are present in an amount between about 0.01% and 1.0% (w/v), or about 0.01% and 0.1% (w/v). In one embodiment, eucalyptol is present at an amount of between about 0.08% and 0.10% (w/v), or about 0.092% (w/v); menthol is present at an amount between about 0.03% and 0.05% (w/v), or about 0.042% (w/v); methyl salicylate is present at an amount between about 0.05% and 0.07% (w/v), or about 0.06% (w/v); and thymol is present at an amount between about 0.05% and 0.07% (w/v), or about 0.062 or 0.064% (w/v).

In one embodiment of the disclosure, the compositions also contain an alcohol such as ethanol. In one embodiment, ethanol helps to solubilize the at least one active ingredient, and is also an anti-septic within the oral cavity. Alcohols, such as ethanol, can also have an astringent or bitter taste for which it is desirous to mask the taste. In one embodiment, the sucralose and saccharin in combination help to mask the taste of compositions containing ethanol. In one embodiment, an alcohol such as ethanol is present in an amount from between about 0% to about 40% (w/v), or about 0% to about 25% (w/v), or less than about 40%, or less than about 25%. In one embodiment, the ethanol is present in an amount of about 17.5% (w/v).

In another embodiment, the compositions of the disclosure further comprise a fluoride compound. In one embodiment, the fluoride compound is sodium fluoride present at an amount of between about 0.01% (w/v) to about 0.05% (w/v), or about 0.02% (w/v). In one embodiment, the fluoride ion is present at an amount of between about 0.01% (w/v) to about 0.05% (w/v), or about 0.02% (w/v).

In another embodiment, the orally acceptable excipient comprises a surfactant, flavoring agents, other anti-bacterial or anti-septic agents, preservatives, dyes, or combinations thereof.

In one embodiment, the anti-bacterial or anti-septic agent is cetylpyridinium chloride present at an amount of between about 0.02% (w/v) to about 0.10% (w/v).

In one embodiment, the surfactant is a non-ionic surfactant. In a further embodiment, the non-ionic surfactant is poloxamer 407 and is present in an amount between about 0.1% and 1.0% (w/v).

In another embodiment, the preservative is sodium benzoate, benzoic acid or combinations thereof present in an amount between about 0.1% to about 1% (w/v).

The present disclosure also includes an anticariogenic oral composition comprising:
 (i) water;
 (ii) ethanol;
 (iii) sucralose;
 (iv) sodium saccharine;
 (v) at least one active ingredient having a bitter taste selected from eucalyptol, menthol, methyl salicylate, and thymol, or combinations thereof; and
 (vi) optionally, other orally acceptable excipients as defined in any of the above paragraphs;
 wherein the composition contains less than 1% (w/v) of a sugar or sugar alcohol.

The present disclosure also includes an oral composition consisting essentially of, or consisting of:
 (i) water;
 (ii) ethanol;
 (iii) sucralose;
 (iv) sodium saccharine;
 (v) at least one active ingredient having a bitter taste selected from eucalyptol, menthol, methyl salicylate, and thymol, or combinations thereof; and
 (vi) optionally, other orally acceptable excipients as defined in any of the above paragraphs;
 wherein the composition contains less than 1% (w/v) of a sugar or sugar alcohol.

In one embodiment, the saccharin and sucralose are present in a ratio of between about 2:1 to about 1:1.

In another embodiment, the composition contains less than about 5.0% (w/v), or less than about 2.0% (w/v), or less than about 1.0% (w/v), or less than about 0.5% (w/v), or less than about 0.1% (w/v) of a sugar or sugar alcohol. In another embodiment, the composition also contains less than about 5.0% (w/v), or less than about 2.0% (w/v), or less than about 1.0% (w/v), or less than about 0.5% (w/v), or less than about 0.1% (w/v) of a polyhydric alcohol, such as glycerin. In a further embodiment, the composition is substantially free of a sugar or sugar alcohol. In another embodiment, the composition is free of a sugar or sugar alcohol. In a further embodiment, the composition is substantially free of a polyhydric alcohol. In another embodiment, the composition is free of a polyhydric alcohol. In one embodiment, the sugar alcohol is sorbitol, xylitol, or maltitol. In another embodiment, the polyhydric alcohol is glycerin or propylene glycol.

In one embodiment, the saccharin and sucralose are present in a ratio of between about 5:1 to about 1:1. In another embodiment, the saccharin and sucralose are present in a ratio of between about 2:1 to about 1:1.

In another embodiment, the sucralose is present at an amount of less than 2.0% (w/v), or less than 1.0% (w/v), for example between about 0.001% to about 1.0% (w/v). In a further embodiment, the saccharin is present at an amount of less than 2.0% (w/v), or less than 1.0% (w/v), for example between about 0.001% to about 1.0% (w/v). In one embodiment, the sodium saccharin is present in an amount of about 0.15% (w/v). In another embodiment, the sucralose is present in an amount of about 0.075% (w/v).

In one embodiment, the ethanol is present in an amount from between about 0% to about 40% (w/v), or about 0% to about 25% (w/v), or less than about 40%, or less than about 25%. In one embodiment, the ethanol is present in an amount of about 17.5% (w/v).

In another embodiment, the essential oils are present in an amount of less than about 1.0% (w/v). In another embodiment, the essential oils are present in an amount between about 0.01% and 1.0% (w/v), or about 0.01% and 0.1% (w/v). In one embodiment, eucalyptol is present at an amount of between about 0.08% and 0.10% (w/v), or about 0.092% (w/v); menthol is present at an amount between about 0.03% and 0.05% (w/v), or about 0.042% (w/v); methyl salicylate is present at an amount between about 0.05% and 0.07% (w/v), or about 0.06% (w/v); and thymol is present at an amount between about 0.05% and 0.07% (w/v), or about 0.064% (w/v).

The present disclosure also includes an oral composition comprising, consisting essentially of, or consisting of:

(i) water;
(ii) ethanol;
(iii) sucralose present at an amount of between about 0.05% to about 0.1% (w/v);
(iv) sodium saccharine present at an amount of between about 0.1% to about 0.2% (w/v);
(v) eucalyptol present at an amount between about 0.08% and 0.10% (w/v);
(vi) menthol present at an amount between about 0.03% and 0.05% (w/v),
(vii) methyl salicylate present at an amount between about 0.05% and 0.07% (w/v),
(viii) thymol present at an amount between about 0.05% and 0.07%; and
(vi) optionally, other orally acceptable excipients as defined in any of the above paragraphs;
wherein the composition contains less than 5% (w/v), or less than 2% (w/v), or less than 1% (w/v), or less than 0.1% (w/v) of a sugar or sugar alcohol.

In one embodiment, the composition is substantially free, or free, of sugars or sugar alcohols.

In another embodiment of the disclosure, the anticariogenic oral care compositions are dry powder compositions which are reconstituted in water to provide cavity preventing compositions. In one embodiment, the dry powder compositions comprise
(i) sucralose;
(ii) saccharin;
(iii) at least one active ingredient having a bitter taste; and
(iv) optionally, orally acceptable excipients as defined in any of the above paragraphs,
wherein the dry powder composition contains less than 1% (w/v) of a sugar or sugar alcohol.

In another embodiment, the dry powder composition contains less than about 5.0% (w/v), or less than about 2.0% (w/v), or less than about 1.0% (w/v), or less than about 0.5% (w/v), or less than about 0.1% (w/v) of a sugar or sugar alcohol. In another embodiment, the dry powder composition also contains less than about 5.0% (w/v), or less than about 2.0% (w/v), or less than about 1.0% (w/v), or less than about 0.5% (w/v), or less than about 0.1% (w/v) of a polyhydric alcohol, such as glycerin. In a further embodiment, the dry powder composition is substantially free of a sugar or sugar alcohol. In another embodiment, the dry powder composition is free of a sugar or sugar alcohol. In a further embodiment, the dry powder composition is substantially free of a polyhydric alcohol. In another embodiment, the dry powder composition is free of a polyhydric alcohol. In one embodiment, the sugar alcohol is sorbitol, xylitol, or maltitol. In another embodiment, the polyhydric alcohol is glycerin or propylene glycol.

In one embodiment, the saccharin and sucralose are present in a ratio of between about 5:1 to about 1:1. In another embodiment, the saccharin and sucralose are present in a ratio of between about 2:1 to about 1:1.

In another embodiment, the sucralose is present at an amount of less than 2.0% (w/v), or less than 1.0% (w/v), for example between about 0.001% to about 1.0% (w/v). In a further embodiment, the saccharin is present at an amount of less than 2.0% (w/v), or less than 1.0% (w/v), for example between about 0.001% to about 1.0% (w/v). In one embodiment, the sodium saccharin is present in an amount of about 0.15% (w/v). In another embodiment, the sucralose is present in an amount of about 0.075% (w/v).

In another embodiment, the dry powder compositions of the disclosure comprise at least one active ingredient having a bitter or unpleasant taste for which it is desired to mask the taste of the ingredient. In one embodiment, the at least one active ingredient is a bitter-tasting anti-bacterial or antiseptic agent. In one embodiment, the active ingredient is an essential oil or extract, or compound found in essential oils, which may have anti-bacterial activity, for example, eucalyptol, menthol, methyl salicylate, thymol, tea tree oil, peppermint oil, *eucalyptus* oil, thyme oil, spearmint oil, wintergreen oil, grapefruit seed extract, or combinations thereof. In another embodiment, the essential oils are present in an amount of less than about 1.0% (w/v). In another embodiment, the essential oils are present in an amount between about 0.01% and 1.0% (w/v), or about 0.01% and 0.1% (w/v). In one embodiment, eucalyptol is present at an amount of between about 0.08% and 0.10% (w/v), or about 0.092% (w/v); menthol is present at an amount between about 0.03% and 0.05% (w/v), or about 0.042% (w/v); methyl salicylate is present at an amount between about 0.05% and 0.07% (w/v), or about 0.06% (w/v); and thymol is present at an amount between about 0.05% and 0.07% (w/v), or about 0.064% (w/v).

In one embodiment, the dry powder composition may be in the form of a loose powder that is simply reconstituted in water. In another embodiment, the dry powder composition is in the form of a capsule or tablet which is dissolved and reconstituted in water.

(III) Prevention of Cavities

The present disclosure also includes a method for the prevention of cavities using the oral care compositions of the disclosure. In one embodiment, there is included a method for the prevention of cavities comprising administering an effective amount of any of the above defined oral compositions to the oral cavity of a person in need thereof.

In another embodiment, there is also included a use of any of the above defined oral compositions for the prevention of cavities.

In one embodiment, the compositions may be used as a daily rinse for the prevention of cavities. In another embodiment, the compositions are used one or more times every day for the prevention of cavities.

The following non-limiting examples are illustrative of the present application:

EXAMPLES

Example 1—Preparation of Oral Composition

The following components were combined in an aqueous solution to prepare an oral anticariogenic composition: eucalyptol (0.092% w/v); menthol (0.043% w/v); methyl salicylate (0.065% w/v); thymol (0.063% w/v); ethyl alcohol (20.2%); sodium saccharin (0.15% w/v); sucralose (0.075% w/v); Poloxamer 407 (0.8% w/v); sodium benzoate (0.1% w/v); benzoic acid (0.1% w/v). The composition further contained other dyes and flavors. The pH of the formulation was 4.26. The refractive index of the composition was 1.3460 and the density was 0.970 g/ml.

Example 2—Comparison of Oral Composition with Other Formulation

The anticariogenic composition prepared in Example 1 was compared to a known oral rinse (LISTERINE®), which contains the following ingredients: eucalyptol (0.092% w/v); menthol (0.042% w/v); methyl salicylate (0.060% w/v); thymol (0.064% w/v); ethyl alcohol (21.6%); sorbitol (14%); Poloxamer 407; sodium benzoate; and benzoic acid. The results of the comparison are shown in Table 1. As clearly indicated in Table 1, the composition of Example 1 is comparable to Listerine® in its flavor profile, flavor intensity and mouthfeel. Listerine® contains 14% sorbitol which is present to mask the bitter taste of the essential oils. The results in Table 1 indicate that the composition of the disclosure containing a combination of saccharin and sucralose are able to mask the taste of the bitter tasting active ingredients without the need of other sugars or sugar alcohols.

While the present application has been described with reference to what are presently considered to be the preferred examples, it is to be understood that the application is not limited to the disclosed examples. To the contrary, the present application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

Comparison of Sensory Similarities of a Composition of the Disclosure

| Property/Physical Characteristic of Composition | Listerine ® Brand Mouthwash | Composition of Example1 Sensory Similarity Rating Scale 0 = very different 8 = identical. A rating of 6 or higher is considered to be comparable. |
| --- | --- | --- |
| Color/Appearance | Bright green with a yellow hue, glossy thin liquid | 7 (Comparable to Listerine ®) |
| Clarity | Clear | 8 (Comparable to Listerine ®) |
| Odor | Sweet, alcohol, *eucalyptus*, mint, menthol | 7 (Comparable to Listerine ®) |
| Flavor | Sweet, alcohol, *eucalyptus*, menthol, mint, bitter | 7 (Comparable to Listerine ®) |
| Flavor Intensity (1-None to 5- Very Strong) | 4 | 4 |
| Mouthfeel | Burning, cooling, numbing, tingling, astringent | 6 (Comparable to Listerine ®) |

The invention claimed is:

1. An anticariogenic oral composition, comprising:
 a) water;
 b) sucralose;
 c) saccharin; and
 d) at least one active ingredient having a bitter taste, wherein the active ingredient is eucalyptol, menthol, methyl salicylate, thymol, or a combination thereof; and
 e) optionally, orally acceptable excipients,
wherein the composition is a mouthwash or an oral rinse, and the composition contains less than about 1% (w/v) of a sugar or sugar alcohol, and wherein the saccharin and sucralose are present in a ratio of 2:1 to mask the bitter taste of the active ingredient.

2. The oral composition of claim 1, wherein the composition contains less than 0.5% (w/v) of a sugar or sugar alcohol.

3. The oral composition of claim 2, wherein the composition is substantially free of a sugar or sugar alcohol.

4. The oral composition of claim 3, wherein the sugar alcohol is sorbitol, xylitol, or maltitol.

5. The oral composition of claim 1, wherein the composition contains less than 1.0% (w/v) of a polyhydric alcohol.

6. The oral composition of claim 1, wherein the saccharin is sodium saccharin.

7. The oral composition of claim 1, wherein the sucralose is present at an amount of between about 0.001% to about 1.0% (w/v).

8. The oral composition of claim 1, wherein the saccharin is present at an amount of between about 0.001% to about 1.0% (w/v).

9. The oral composition of claim 1, wherein composition further comprises ethanol and is present in an amount from between about 0% to about 25% (w/v).

10. The oral composition of claim 1, wherein the orally acceptable excipient comprises a surfactant, flavoring agent, anti-bacterial agent, preservative, dye, or combinations thereof.

11. The oral composition of claim 10, wherein the surfactant is a non-ionic surfactant which is poloxamer 407 and is present in an amount between about 0.1% and 1.0% (w/v).

12. The oral composition of claim 10, wherein the preservative is sodium benzoate, benzoic acid or combinations thereof present in an amount between about 0.1% to about 1% (w/v).

13. An anticariogenic oral composition comprising:
 a) water;
 b) ethanol;
 c) sucralose present at an amount of between about 0.05% to about 0.1% (w/v);
 d) sodium saccharin present at an amount of between about 0.1% to about 0.2% (w/v);
 e) eucalyptol present at an amount between about 0.08% and 0.10% (w/v);
 f) menthol present at an amount between about 0.03% and 0.05% (w/v),
 g) methyl salicylate present at an amount between about 0.05% and 0.07% (w/v), and
 h) thymol present at an amount between about 0.05% and 0.07%;
wherein the composition is a mouthwash or an oral rinse, and the composition contains less than less than about 1% (w/v) of a sugar or sugar alcohol, and wherein the saccharin and sucralose are present in a ratio of 2:1 to mask the bitter taste of eucalyptol, menthol, methyl salicylate, thymol, or a combination thereof.

14. A method for the prevention of cavities comprising administering an effective amount of the anticariogenic oral composition of claim 1 to the oral cavity of a person in need thereof.

* * * * *